(12) United States Patent
Zhang et al.

(10) Patent No.: US 9,320,280 B2
(45) Date of Patent: Apr. 26, 2016

(54) **METHODS AND COMPOSITIONS FOR DETERRING FEEDING/REPELLING THE BROWN MARMORATED STINK BUG (BMSB), *HALYOMORPHA HALYS***

(71) Applicant: The United States of America, as Represented by the Secretary of Agriculture, Washington, DC (US)

(72) Inventors: Aijun Zhang, Ellicott City, MD (US); Christina Harris, Silver Spring, MD (US); Tracy C. Leskey, Shepherdstown, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 349 days.

(21) Appl. No.: 13/761,320

(22) Filed: Feb. 7, 2013

(65) Prior Publication Data
US 2014/0256825 A1 Sep. 11, 2014

Related U.S. Application Data

(60) Provisional application No. 61/602,143, filed on Feb. 23, 2012.

(51) Int. Cl.
| | |
|---|---|
| *A01N 35/06* | (2006.01) |
| *A01N 27/00* | (2006.01) |
| *A01N 35/02* | (2006.01) |
| *A01N 45/02* | (2006.01) |

(52) U.S. Cl.
CPC ..................................... *A01N 45/02* (2013.01)

(58) Field of Classification Search
None
See application file for complete search history.

(56) References Cited

U.S. PATENT DOCUMENTS

| 7,824,668 | B2 | 11/2010 | McKibben | |
|---|---|---|---|---|
| 2008/0044375 | A1 | 2/2008 | McKibben | |
| 2008/0263938 | A1 | 10/2008 | Schneidmiller | |
| 2009/0018192 | A1* | 1/2009 | Zhang et al. | 514/546 |

OTHER PUBLICATIONS

Moraes et al., The Chemical Volatiles (Semiochemicals) Produced by Neotropical Stink Bugs (Hemiptera: Pentatomidae), Neotropical Entomology, 37(5), 2008, pp. 489-505.*
Krell et al., "Chemical Defesnse in the Stink Bug Cosmopepla bimaculata", Journal of Chemical Ecology, 25(11), 1999, pp. 2477-2494.*
Aldrich, J.R. et al Pentatomid Natural Prodcuts Chemistry and Morphology of the III-IV Dorsal Abdominal Glands of Adults, J. Chem. Ecol., 1978, pp. 161-172, vol. 4 (2).
Aligiannis, N. et al., Essential Oils of Phlomis Species Growing in Greece: Chemical Composition and Antimicrobial Activity, Flavour and Fragrance Journal, 2004, pp. 320-324, vol. 19.
Aoyagi, H. et al., Measurement of Fresh and Dry Densities of Suspended Plant Cells and Estimation of Their Water Content, Journal of Fermentation and Bioengineering, 1992, pp. 490-496, vol. 73 (6).
Ashour, M.L. et al., Chemical Composition and Biological Activity of the Essential Oil Obtained from Bupleurum Marginatum (Apiaceae), Journal of Pharmacy and Phamacology, 2009, pp. 1-9, vol. 61.
Baser, K.H.C. et al., Essential Oil of Cymbocarpum Wiedemannii Boiss., J. Essent. Oil Res., 1999, pp. 679-680, vol. 11.
Baser, K.H.C. et al., Composition of the Essential Oil of Chaerophyllum Macropodum Boiss. Fruits Obtained by Microdistillation, J. Essent. Oil Res., 2006, pp. 515-517, vol. 18.
Blum, M.S. et al., n-Tridecane and trans-2-Heptenal in Scent Gland of the Rice Stink Bug Oebalus pugnax (F.), Science, 1960, pp. 1480-1481, vol. 132.
Borges, M. et al., Long-Range Mate Location and Close-Range Courtship Behaviour of the Green Stink Bug, Nezara Viridula and its Mediation by Sex Pheromones, Entomol. Exp. Appl., 1987, pp. 205-212, vol. 44.

(Continued)

*Primary Examiner* — Bethany Barham
*Assistant Examiner* — Melissa Javier
(74) *Attorney, Agent, or Firm* — G. Byron Stover; John D. Fado

(57) ABSTRACT

Compositions (feeding deterrent/repellent for *Halyomorpha halys*) containing at least two compounds selected from tridecane, E-2-decenal, isolongifolanone, isolongifolenone, and at least one isolongifolenone analog having the following formula:

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. Also methods for deterring feeding/repelling *Halyomorpha halys* involving treating an object or area with a *Halyomorpha halys* deterring feeding/repelling effective amount of at least one compound selected from the above compounds.

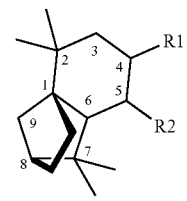

1 Claim, 15 Drawing Sheets

(56) References Cited

OTHER PUBLICATIONS

Brahmi, F. et al., Fatty Acid Composition and Biological Activities of Volatiles from Fruits of Two Tunisian Olive Clutivars, International Journal of Food Science and Technology, 2011, pp. 1316-1322, vol. 46.
Calam, D.H. et al., Identification and Functions of Secretion from the Posterior Scnt Gland of Fifth Instar Larva of the Bug Dysdercus Intermedius, J. Insect Physiol., 1968, pp. 1147-1158, vol. 14.
Chen, G. et al., Aroma-Active Compounds of Beijing Roast Duck, Flavour Fragr. J., 2009, pp. 186-191, vol. 24.
Cho, I.H. et al., Volatiles and Key Odorants in the Pileus and Stipe of Pine-Mushroom (Tricholoma Matsutake Sing.), Food Chemistry, 2008, pp. 71-76, vol. 106.
Christlbauer, M. et al., Evaluation of the Key Aroma Compounds in Beef and Pork Vegetable Gravies a La Chef by Stable Isotope Dilution Assays and Aroma Recombination Experiments, Journal f Agricultural and Food Chemistry, 2011, pp. 13122-13130, vol. 59.
Delaquis, P.J. et al., Antilisterial Properties of Cilantro Essential Oil, J. Essent. Oil Res., 2004, pp. 409-414, vol. 16.
Favaro, C.F. et al., Identificaiton of Semiochemicals in Adults and Nymphs of the Stink Bug Pallantia Macunaima Grazia (Hemiptera: Pentatomidae), J. Braz. Chem. Soc., 2011, pp. 58-6, vol. 22 (1).
Fucarino, A. et al., Chemical and Physical Signals Mediating Conspecific and Heterospecific Aggregation Behavior of First Instar Stink Bugs, Journal of Chemical Ecology, 2004, pp. 1257-1269, vol. 30 (6).
Gaffney, J.S. et al., An Improved Procedure for High Purity Gaseous Peroxyacyl Nitrate Production: Use of Heavy Lipid Solvents, Atmospheric Environment, 1984, pp. 215-218; vol. 18 (1).
Ghatorae, A.S. et al., Inactivatio of Enzymes by Organic Solvents: New Technique with Well-Defined Interfacial Area, Biotechnology and Bioengineering, 1994, pp. 331-336, vol. 43.
Gough, A.J.E. et al., Multichemical Defense of Plant Bug Hotea Gambiae (Westwood) (Heteroptera: Scutelleridae) Sesquiterpenoids from Abdominal Gland in Larvae, Journal of Chemical Ecology, 1985, pp. 343-352, vol. 11 (3).
Ho, H.-Y. et al., Compounds in Metathoracic Glands of Adults and Dorsal Abdominal Glands of Nymphs of the Stink Bugs, Chlorochroa Uhleri, C. Sayi, and C. Ligata (Hemiptera: Pentatomidae), Zoological Studies, 2001, pp. 193-198, vol. 40 (3).
Ho, H.-Y. et al., Semiochemicals from the Predatory Stink Bug Eocanthecona Furcellata (Wolff): Components of Metathoracic Gland, Dorsal Abdominal Gland, and Sternal Gland Secretions, Journal of Chemical Ecolgy, 2003, pp. 2101-2114, vol. 29 (9).
Ibrahim, H. et al., Essential Oils of Elettariopsis Curtisii (Zingiberaceae) and their Antimicrobial Activities, Journal of Essential Oil Research, 2009, pp. 464-466, vol. 21.
Kivcak, B. et al., Composition of the Essential Oil of Arbutus Unedo, Chemistry of Natural Compounds, 2001, pp. 445-446, vol. 37 (5).
Kou, R. et al., Alarm Pheromone of Pentatomid Bug, Erthesina Fullo Thunberg (Hemiptera: Pentatomidae), Journal of Chemical Ecology, 1989, pp. 2695-2702, vol. 15 (12).
Krall, B.S. et al., Chemical Defense in the Stink Bug Cosmopepla Bimaculata, Journal of Chemical Ecology, 1999, pp. 2477-2494, vol. 25 (11).
Lockwood, J.A. et al., Bifunctional Pheromone in the First Instar of the Southern Green Stink Bug, Nezara Viridula (L.) (Hemiptera: Pentatomidae): Its Characterization and Interaction with Other Stimuli, Anals of the Entomological Society of America, 1985, pp. 474-479, vol. 78.
Marques, F.A. et al., Identification of Defensive Compounds in Metathoracic Glands of Adulst of the Stink Bug Dichelops Melacanthus (Hemiptera: Pentatomidae), J. Braz. Chem. Soc., 2007, pp. 1242-1246, vol. 18 (6).
Minh, N.T. et al., Volatile Constiuents of Bietnamese Pummelo, Orange, Tangerine and Lime Peel Oils, Flavour and Fragrance Journal, 2002, pp. 164-174, vol. 17.
Moreno, A.O. et al., Effect of Different Extraction Methods on Fatty Acids, Volatile Compounds, and Physical and Chemical Properties of Avocado (Persea Americana Mill.) Oil, J. Agric. Food Chem., 2003, pp. 2216-2221, vol. 51.
Moronkola, D.O. et al., Essential Oil Composition of Gmelina Arobrea Roxb., Verbenaceae, from Nigeria, Journal of Essential Oil, 2009, pp. 264-266, vol. 21.
Nagalakshmi, M.A.H. et al., Essential Oil Constitutes of Melia Dubia, a Wild Relative of Azadirachta Indica Growing in the Eastern Ghats of Peninsular India, Flavour and Fragrance Journal, 2001, pp. 241-244, vol. 16.
Nagnan, P. et al., Fine Structure and Physicochemical Analysis of the Metathoracic Scent Glands of Lincus Malevolus (Rolston) and L. Spurcus (Rolston) (Heteroptera: Pentatomidae), Int. J. Insect Morphol. & Embryol., 1994, pp. 355-370, vol. 23 (4).
Neffati, M. et al., Salinity Impact on Growth, Essential Oil Content and Composition of Coriander (Coriandrum Sativum L.) Stems and Leaves, Journal of Essential Oil Research, 2010, pp. 29-34, vol. 22.
Neffati, M. et al., Changes in Essential Oil and Fatty acid Composition in Coriander (Coriandrum Sativum L.) Leaves Under Saline Conditions, Industrial Crops and Products, 2008, pp. 137-142, vol. 28.
Pareja, M. et al., Inter- and Intraspecific Variation in Defensive Compounds Produced by Five Neotropical Stink Bug Species (Hemiptera: Pentatomidae), Journal of Insect Physiology, 2007, pp. 639-648, vol. 53.
Potter, T.L., Essential Oil Composition of Cilantro, J. Agric. Food Chem. pp. 1824-1826, vol. 44.
Rapior, S. et al., Investigation of Some Volatile Components of Seven Fresh Wild Mushrooms (Basidiomycetes), J. Essent. Oil Res., 1996, pp. 199-201, vol. 8.
Raspotnig, G. et al., Chemistry of the Oil Gland Secretion of Collohmannia Gigantea (Acari: Oribatida), Experimental and Applied Acarology, 2001, pp. 939-946, vol. 25.
Siang, G.H. et al., Hollow Fiber Liquid-Phase Microextraction Coupled with Gas Chromatography-Flame Ionization Detection for the Profiling of Fatty Acids in Vegetable Oils., Journal of Chromatography A, 2010, pp. 8073-8078, vol. 1217.
Sosa-Gomez, D.R. et al., Attachment of Metarhizium Anisopliae to the Southern Green Stink Bug Nezara Viridula Cuticle and Fungistatic Effect of Cuticular Lipids and Aldehydes, Journal of Invertebrate Pathology, 1997, pp. 31-39, vol. 69.
Sturaro, A. et al., A Simple and Fast Sampling Method for the Characterization of Volatile Compounds Released by Nezara Viridula, Chromatographia, 1994, pp. 103-106, vol. 39 (112).
Telci, I. et al., Biomass Yield and Herb Essential Oil Characters at Different Harvest Stages of Spring and Autumn Sown Coriandrum Sativum, Europ. J. Hort. Sci., 2008, pp. 267-272, vol. 73 (6).
Williams, L. et al., Defensive Chemistry of an Aposematic Bug, Pachycoris Stallii Uhler and Volatile Compounds of its Host Plant Croton Californicus Muell.-Arg., Journal of Chemical Ecology, 2001, pp. 203-216, vol. 27 (2).
Witte, V. et al., Structure and Function of Dufour Gland Pheromones from the Crazy ant Paratrechina Longicornis, Chemoecolgy, 2007, pp. 63-69, vol. 17.
Wong, K.C. et al., Essential Oils of Elettariopsis Slahmong C.K. Lim, J. Essent. Oil Res. 2006, pp. 203-205, vol. 18.
Aldrich, J.R. et al., Identification and Attractiveness of a Major Pheromone Component for Nearctic Euschistus spp. Stink Bugs (Heteroptera: Pentatomidae), Environ. Entomol., 1991, vol. 20 (2), pp. 477-483.
Aldrich, J.R. et al., Methyl 2,4,6-decatrienoates Attract Stink Bugs and Tachinid Parasitoids, J. Chem. Ecol., 2007, vol. 33, pp. 801-815.
Gill, S. et al., Brown Marmorated Stink Bug (Halyomorpha halys),IPM Pest Alert, 2010, www.ipmnet.umd.edu.
Gill, S. et al., Brown Marmorated Stink Bug (Halyomorpha halys),IPM Garden Center Fact Sheet, 2011, www.ipmnet.umd.edu.
Khrimian, A., The Geometric Isomers of Methyl-2,4,6-decatrienoate, Including Pheromones of a Least Two Species of Stink Bugs, Tetrahedron, 2005, vol. 61, pp. 3651-3657.

(56) References Cited

OTHER PUBLICATIONS

McBrien, H.L. et al., Sex Attractant Pheromone of the Red-Shouldered Stink Bug Thyanta Pallidovirens: A Pheromone Blend with Multiple Redundant Components, Journal of Chemical Ecology, 2002, vol. 28 (9), pp. 1797-1818.

Millar, J.G., Methyl (2E,4Z,6Z)-Deca-2,4,6-trienoate, a Thermally Unstable, Sex-Specific Compound from the Stink Bug Thyanta Pallidovirens, Tetrahedron Letters, 1997, vol. 38 (46), pp. 7971-7972.

Millar, J.G. et al., Pentatomid Bug Pheromones in IPM: Possible Applications and Limitations, Use of Pheromones and Other Semiochemicals in Integrated Production, IOBC wprs Bulletin, 2002, vol. 25, pp. 1-11.

Moraes, M.C.B. et al., Sex Attractant Pheromone from the Neotropical Red-Shouldered Stink Bug, Thyanta perditor (F.), Journal of Chemical Ecology, 2005, vol. 31 (6), pp. 1415-1427.

Sugie, H. et al., Identification of the Aggregation Pheromone of the Brown-Winged Green Bug, Plautia Stali Scott (Heteroptera: Pentatomidae), Appl. Entomol. Zool., 1996, vol. 31 (3), pp. 427-431.

Zahn, D.K. et al. Identificaiton, Synthesis, and Bioassay of a Male-Specific Aggregation Pheromone form the Harlequin Bug, Murgantia Histrionica, J. Chem. Ecol., 2008, vol. 34, pp. 238-251.

Zhang, Q-H et al., "Murgantiol as a Stink Bug Synergistic Attractant for use Outdoors," U.S. Appl. No. 13/410,124, filed Mar. 1, 2012.

Zhang, Q.-H. et al., Essential Oils as Spatial Repellents for the Brown Marmorated stink Bug, Halyomorpha halys (Stal) (Hemiptera: Pentatomidae), Journal of Applied Entomology, 2013,10 pages.

Aldrich, J.R. et al., Semiochemically Based Monitoring of the Invasion of the Brown Marmorated Stink Bug and Unexpected Attraction of the Native Green Stink Bug (Heteroptera: Pentatomidae) in Maryland, Florida Entomologist, 2009, vol. 92 (3), pp. 483-491.

Gill, The brown marmorated stink bug, Growertalks, Pest Management, 2010, http://ballpublishing.com/GrowerTalks/ViewArticle.aspx?articleid=18206.

Fons, F. et al., Biodiversity of Volatile Organic Compounds from Five French Ferns, Natural Product Communications, 2010, pp. 1655-1658, vol. 5 (10).

Oliver, J.E. et al., Verdediginigsekresies van die Graanstinkluis Macchiademus Diplopterus (Heteroptera: Lygaeidae), Suid-afrikaanse Tydskrif vir Natuurwetenskap en Tegnologie, 1996, pp. 172-174, vol. 15 (4).

Wang, J. et al., Antimicrobial and Antioxidant Activities of the Flower Essential Oil of Halimodendron Halodendron, Natural Product Communications, 2011, pp. 1749-1753, vol. 6 (11).

* cited by examiner

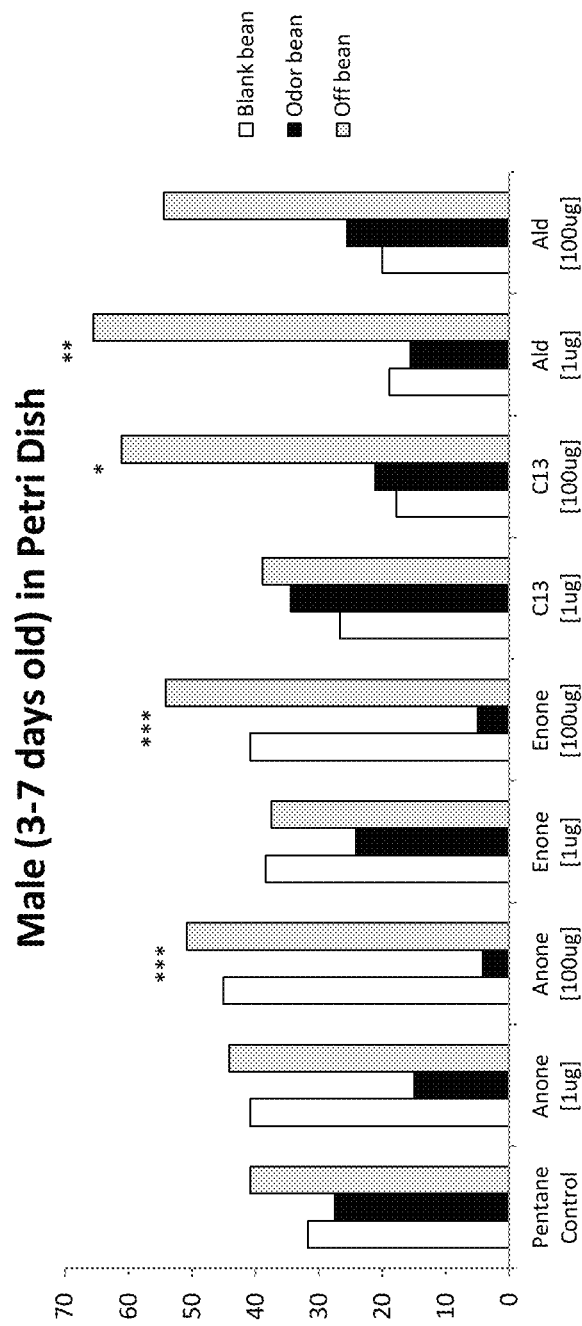

METHODS AND COMPOSITIONS FOR DETERRING FEEDING/REPELLING THE BROWN MARMORATED STINK BUG (BMSB), *HALYOMORPHA HALYS*

BACKGROUND OF THE INVENTION

Compositions (feeding deterrent/repellent for *Halyomorpha halys*) containing at least two compounds selected from tridecane, E-2-decenal, isolongifolanone, isolongifolenone, and at least one isolongifolenone analog having the following formula:

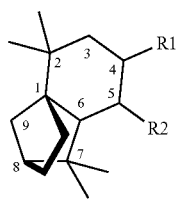

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. Also methods for deterring feeding/repelling *Halyomorpha halys* involving treating an object or area with a *Halyomorpha halys* deterring feeding/repelling effective amount of at least one compound selected from tridecane, E-2-decenal, isolongifolanone, isolongifolenone, and at least one isolongifolenone analog having the following formula:

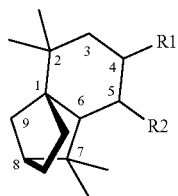

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material.

The brown marmorated stink bug, *Halyomorpha halys* (Stal) (Order Hemiptera: Family Pentatomidae), is an extremely polyphagous insect pest originating from Asia (Funayama, K., Japanese Journal of Applied Entomology and Zoology, 49(4): 265-268 (2005); Funayama, K., Japanese Journal of Applied Entomology and Zoology, 51(3): 238-240 (2007); Son, J, K, et al., Acta Horticulturae, pages 325-330 (2009)). This exotic insect invaded the United States in 2001 (Hoebeke, E. R., and M. E. Carter, Proc. Entomol. Soc. Wash., 105: 225-237 (2003)) and has been detected in 35 states and the District of Columbia, and has been found to feed on over 300 host plants including forest trees, ornamentals, tree fruits, soybean, cotton, and garden vegetables (Hoebeke and Carter 2003; Nielsen, A. L., and G. C. Hamilton, Journal of Economic Entomology, 102: 1133-1140 (2009); Nielsen, A. L., and G. C. Hamilton, Annals of the Entomological Society of America 102: 608-616 (2009); Jacobs, S., Brown marmorated stink bug *Halyomorpha halys*, http://ento.psu.edu/extension/factsheets/brown-marmorated-stink-bug, Feb. 6, 2012). Damage to fruit from *H. halys* in mid-Atlantic States has reached critical levels, causing serious impairment to peach and apple crops, with some growers losing 60 to 100 percent of their yield (Marder, J., Stink Bug Invasion: Is a Wasp the Solution to Save Valued Crops? (2011), http://www.pbs.org/newshour/rundown/2011/05/fighting-the-stink-bug.html, Feb. 6, 2012; Sun-Gazette W., Brown marmorated stink bug update (2011), http://www.sungazette.com/page/content.detail/id/561129/Brown-marmorated-stink-bug-update.html?nav=5014, Feb. 6, 2012; Leskey, T. C., and G. Hamilton, Brown marmorated D.N. 0136.12 stink bug working group meeting summary report (2010), http://projects.ipmcenters.org/Northeastern/FundedProjects/ReportFiles/Pship2010/Pship2010-Leskey-ProgressReport-237195-Meeting-2010_11_17.pdf, Feb. 6, 2012). In addition, *H. halys* is a considerable homeowner nuisance when insects are seeking overwintering sites in the late summer and early fall (Hoebeke and Carter 2003; Nielsen and Hamilton, Annals of the Entomological Society of America, 102: 608-616 (2009)).

Isolongifolenone is a naturally-occurring sesquiterpene isolated from the Tauroniro tree (*Humiria balsamifera*) of South America (Da Silva, T. B. C., et al., Pharm. Biol., 42: 94-97 (2004)). It is an important and well-known compound in the chemical industry. Recently, isolongifolenone and isolongifolenone have been found as novel sesquiterpene repellents of ticks and mosquitoes (Zhang, A., et al., U.S. Pat. No. 7,378,557 B1; Zhang, A., et al., J. Med. Entomol., 46: 100-106 (2009); Zhang, A., et al., U.S. Pat. No. 7,579,016; Carroll, J. F., et al., (2011) Using lone star ticks, *Amblyomma americanum* (Acari: Ixodidae), in in vitro laboratory bioassays of repellents: dimensions, duration, and variability, In: Paluch, G., and J. Coats, eds, Recent Developments in Invertebrate Repellents, ACS Symposium Series, Washington, D.C.: American Chemical Society, pp. 97-120) and can be easily synthesized from a precursor widely distributed in pine oil (Wang, S., and A. Zhang, Organic Preparations and Procedures International, 40: 405-410 (2008)).

Currently, there are no useful tools for successful management of *H. halys*. Thus a feeding deterrent/repellent would be useful for crop protection and management of this invasive species.

SUMMARY OF THE INVENTION

Compositions (feeding deterrent/repellent for *Halyomorpha halys*) containing at least two compounds selected from tridecane, E-2-decenal, isolongifolanone, isolongifolenone, and at least one isolongifolenone analog having the following formula:

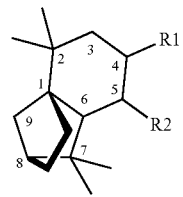

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. Also methods for deterring feeding/repelling *Halyomorpha halys* involving treating an object or area with a *Halyomorpha halys* deterring feeding/repelling effective amount of at least one compound selected from tridecane, E-2-decenal, isolongifolanone, isolongifolenone, and at least one isolongifolenone analog having the following formula:

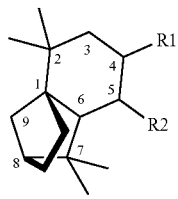

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

FIG. 4 shows the average male-specific compounds (pheromone), C-13, and E-2-decenal per day for single and multiple adult males as described below. Average and standard error of the male specific compounds, C-13, and aldehyde (E-2-decenal) were calculated for single- and multiple-male chambers using data collected in 24-hour increments throughout 2011 on 13-90 day-old adult male *H. halys*. Treatments were compared using ANOVA of log-transformed data with repeated measures.

FIGS. 6A-E show the effectiveness of different repellent compounds on deterring *H. halys* feeding on green beans in closed-air petri dish tests as described below. Young adult males showed a slight preference for pentane-treated green beans over the untreated control bean. Based on these results, we chose pentane as the solvent for subsequent repellent assays in petri dishes to emphasize repellency effects. Repellents were dissolved in pentane and applied to filter paper under green bean in 75 ul applications which yielded a 1-inch diameter circle of repellent under the bean. FIG. 6A shows that starved nymphs ($3^{rd}$ stage) were significantly less likely to feed on beans treated with 100 μg islongifolanone as well as 1 μg or 100 μg concentrations of islongifolenone and C-13. FIG. 6B shows that young adult males (ages 3-7 days into adult stage) were significantly less likely to feed on 100 μg concentrations of isolongifolanone, isolongifolenone, and C-13, as well as 1 μg concentrations of E-2-decenal. FIG. 6C shows that young adult females were significantly less likely to feed on 100 μg concentrations of isolongifolanone and isolongifolenone. FIG. 6D shows that old adult males (ages 13-23 days) were significantly less likely to feed on beans treated with 100 μg isolongifolanone or 1 μg C-13, and FIG. 6E shows that old adult females were significantly less likely to feed on 100 μg concentrations of isolongifolanone and isolongifolenone. Asterisks above groups of bars indicate the significance of the three behavioral observations (blank bean, odor bean, off bean) relative to the pentane control shown as the first set of bars in the figure, with p<0.05 (*), p<0.01 (), and p<0.001 (*), n=30-40 for adults, 40-80 for nymphs.

In FIG. 7A, the average number of nymphs ($3^{rd}$ stage) feeding on peaches over 8 hours of observations was lower for all compounds and combinations of compounds relative to the Tween and $H_2O$ controls, except for the aldehyde/C-13 combination. The three-component blend of equal concentrations isolongifolanone+isolongifolenone+C-13 yielded the highest repellency. Statistical analysis of ANOVA (Model: Insects on fruit=Treatment, Rep (Treatment) were as follows:

for nymphs: $F_{10,830}$-41.82, p<0.0001. There were 15 nymphs per cage, and 4-28 reps tested.

Figure 7A:
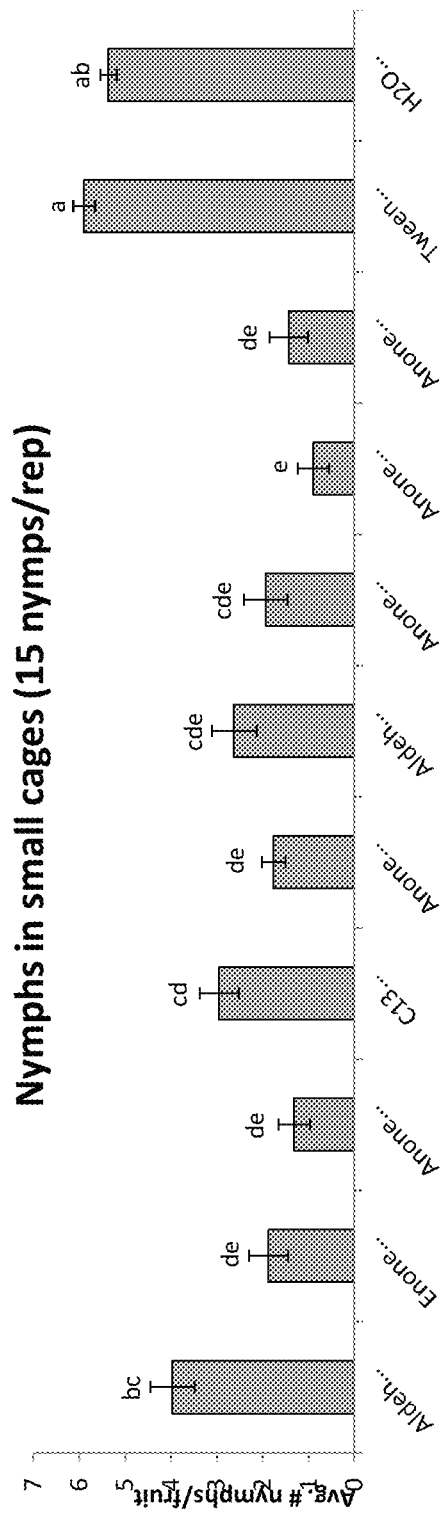
FIGS. 7A-D show the effectiveness of both individual and combined compounds at deterring *H. halys* feeding in open-air small cage bioassays as described below. Letters above bars indicate significance of treatment relative to other treatments; shared letters are not significantly different from each other.
Figure 7B:
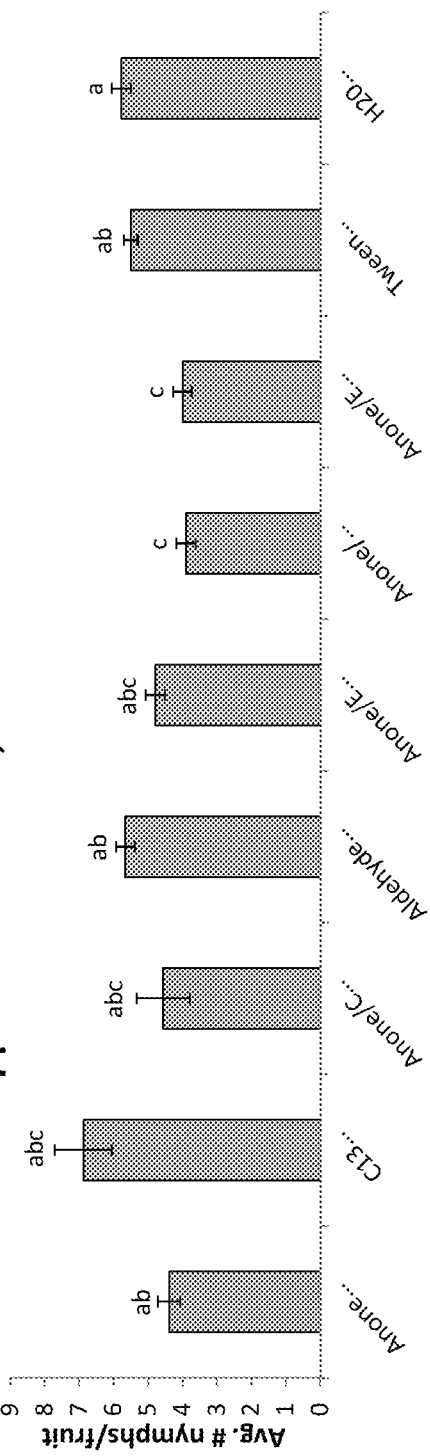
Figure 7C:
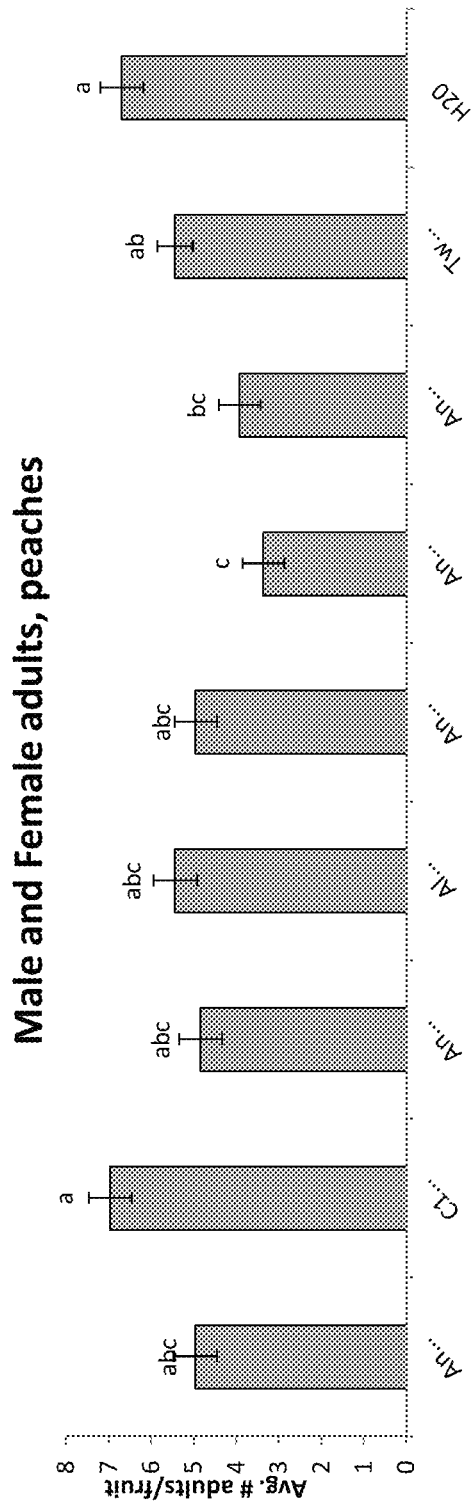
Figure 7D:
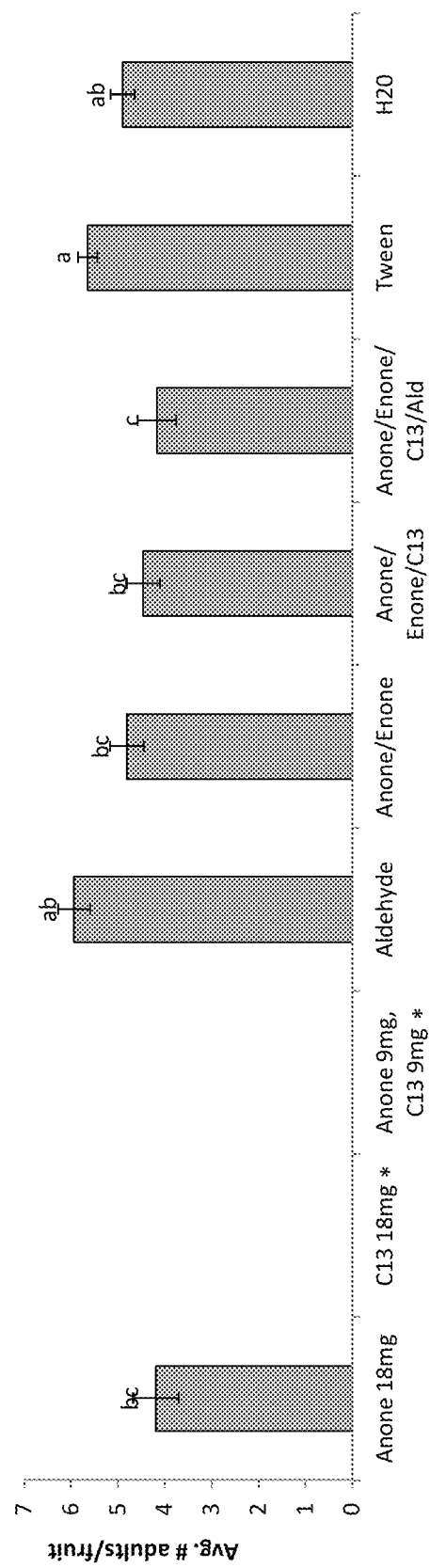

FIGS. 7B-D show male and female behavior in small cages for repellents tested on peaches (FIG. 7C) and apples (7D) as described below. Results did not significantly differ by fruit or age group tested, so data was combined in FIG. 7B. The 3- and 4-component blends of isolongifolanone+isolongifolenone+C-13, and isolongifolanone+isolongifolenone+C-13+Aldehyde were significantly more repellent to starved male and female adults than the Tween and $H_2O$ control. C-13 and Anone/C-13 were not tested for adults in apples. Repeated-measures ANOVA showed a significant effect for repellent treatments in peaches (p<0.0001), apples (p<0.0001), and combined apples and peaches data (p=0.007). There were 10 male or female adults per cage and 2-6 reps conducted per sex (4-12 reps total).

DETAILED DESCRIPTION OF THE INVENTION

Disclosed are compositions (feeding deterrent/repellent for *Halyomorpha halys*) containing at least two compounds selected from tridecane, E-2-decenal, isolongifolanone, isolongifolenone, and at least one isolongifolenone analog having the following formula:

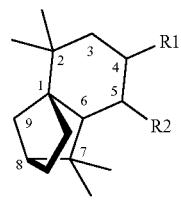

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. Also disclosed are methods for deterring feeding/repelling *Halyomorpha halys* involving treating (or exposing) an object or area (e.g., field, orchard) with a *Halyomorpha halys* deterring feeding/repelling effective amount of at least one compound selected from tridecane, E-2-decenal, isolongifolanone, isolongifolenone, and at least one isolongifolenone analog having the following formula:

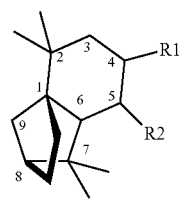

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material.

Generally the isolongifolenone analogs have the following formula:

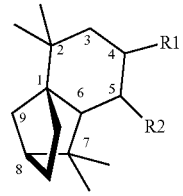

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); optionally there is a double bond between carbons 5 and 6 and $R_2$ is hydrogen. Preferably $R_1$ or $R_2$ are hydrogen (in other words, $R_1$ can be hydrogen or $R_2$ can be hydrogen or both $R_1$ and $R_2$ can be hydrogen). Preferably $R_1$ and $R_2$ are not both hydrogen (in other words if $R_1$ is hydrogen then $R_2$ is not hydrogen or if $R_2$ is hydrogen then $R_1$ is not hydrogen).

The isolongifolenone analogs can be a (1R,8S)-2,2,7,7-tetramethyltricyclo[6.2.1.0$^{1,6}$]undec-5-ene having the formula:

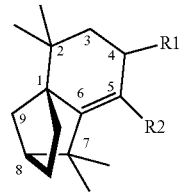

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen.

The isolongifolenone analogs can be a (1S,8S)-2,2,7,7-tetramethyltricyclo[6.2.1.0$^{1,6}$]undecane having the formula:

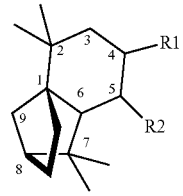

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen; and optionally a carrier or carrier material.

The isolongifolenone analogs can be a tricyclo(1S,8S)-2,2,7,7-tetramethyltricyclo[6.2.1.0$^{1,6}$]undecane having the formula:

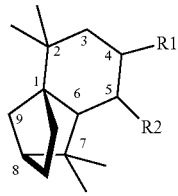

wherein $R_2$ is an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_1$ is hydrogen; and optionally a carrier or carrier material.

The isolongifolenone analogs can be a (1S,8S)-2,2,7,7-tetramethyltricyclo[6.2.1.0$^{1,6}$]undecane having the formula:

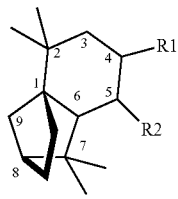

wherein $R^1$ is an oxygen, a $C_{1-10}$ alcohol (straight or branched), aldehyde, alkyl, ether (e.g. methanol, ethanal, 4-methylhexane, heptyloxymethane), or esters of said with a $C_{1-10}$ saturated or unsaturated, straight or branched acid (e.g., formic acid, acetic acid, 2-methylbutyric acid, 3-methyl-2-butenoic acid) and $R^2$ is an oxygen, a $C_{1-10}$ alcohol (straight or branched), aldehyde, alkyl, ether (e.g. methanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); and optionally a carrier or carrier material.

Figure 5:
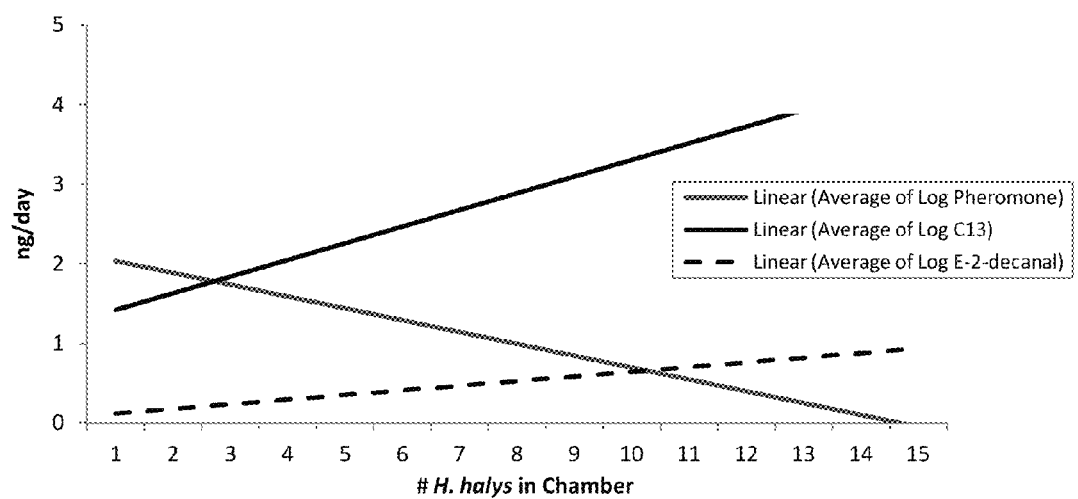
FIG. 5 shows the amount of pheromone, C-13, and E-2-decenal present by number of *H. halys* adults in chamber as described below. This was analyzed with data collected in 24-hour increments throughout 2011 on 13-90 day-old adult male *H. halys*, with log-transformed data using repeated measures ANOVA for Compound=subject, # males (subject). Pheromone $F_{71,1}$-6.634; p<0.0001; C-13 F71,1=5.701; p=0.001; Aldehyde F71,1=1.617; p=0.003. Regression equations: Pheromone=−0.17×+2.52; C-13=0.22×+1.15; Aldehyde=−0.773×+0.290. The relationship between C-13 and the male-produced male-specific compounds was analyzed via ANOVA using pairwise correlations, p<0.0001. The C-13 and male specific compounds interaction overlaps at 2.50 males.

Preferably the isolongifolenone analogs are one of the compounds in FIG. 5 in U.S. Pat. No. 7,579,016 (excluding isolongifolenone).

The optical isomers of isolongifolenone analogs could be (+)- or (−)-; depending on the starting material isolongifolene or isolongifolene.

The isolongifolenone analogs were synthesized according to known methods: Synthesis of dihydroisolongifolenone (J4-120A) (Prahlad, J. R., et al., Tetrahedron Lett., 5: 417-427 (1964); Ranganathan, R., et al., Tetrahedron, 26: 621-630 (1970)). Synthesis of isolongifolenyl alcohol (J4-120B) (Curtis, A. J., et al., GB Patent No. 1,256,535 (1971); Banthorpe, D. V., Tetrahedron Lett., 36: 3865-3868 (1972); Pickenhagen, W., and D. Schatkowski, U.S. Pat. No. 6,734,159 B2 (2004)). Synthesis of dihydroisolongifolenyl alcohol (J4-120E), same procedure as J4-120B. Synthesis of dihydroisolongifolenyl alcohol acetate (J4-120C) (Raucher, S., et al., J. Am. Chem. Soc., 103: 1853-1855 (1981); Pinheiro, S., et al., Tetrahedron Asymmetry, 11:3495-3502 (2000)). Synthesis of isolongifolenyl alcohol acetate (J4-120D), same procedure as J4-120C. Synthesis of isolongifolanone (J4-120F) (U.S. Pat. No. 5,426,095); it was obtained from Bedoukian Research Inc. as a gift.

The carrier or carrier material may be, for example, agronomically, physiologically, or pharmaceutically acceptable carriers or carrier materials. An insect repellent is any compound or composition which deters insects from an object or area. Thus, the term "repelling" is defined as eliciting insects (e.g., male *Halyomorpha halys*) to make oriented movements away from a source of a chemical repellent (Dethier, V. L., et al., J. Econ. Ent., 53: 134-136 (1960)), and also includes inhibiting feeding by insects when a chemical is present in a place where insects would, in the absence of the chemical, feed.

The feeding deterrent/repellent of the present invention may be applied with a carrier component. The carrier component can be a liquid or a solid material. As is known in the art, the vehicle or carrier to be used refers to a substrate such as water, membranes, hollow fiber, microcapsule, cigarette filters, gel, polymers, or the like. All of these substrates have been used to release insect feeding deterrent/repellents in general and are well known in the art. The carrier or carrier material as used herein is defined as not including the body of an insect (e.g., *Halyomorpha halys*).

A repellent is any compound or composition which deters insects from biting and feeding on a host. Thus, the term "repelling" is defined as inhibiting feeding by insects when a chemical is present in a place where insects (e.g., *Halyomorpha halys*) would, in the absence of the chemical, feed, and it also includes causing insects (e.g., *Halyomorpha halys*) to make oriented movements away from a source of a chemical repellent (Dethier, V. L., et al., J. Econ. Ent., 53: 134-136 (1960)). Thus, the term "repelling" also includes reducing the number of insect (e.g., *Halyomorpha halys*) bites on a treated area or object (e.g., fruit skin which has been treated topically with the compositions or compounds of the present invention) when compared to the same area or object which is untreated, and the term "repelling" also includes causing insects (e.g., *Halyomorpha halys*) to make oriented movements away from a treated area or object (e.g., fruit skin which has been treated topically with the compositions or compounds of the present invention) when compared to the same area or object which is untreated. The amount of the feeding deterrent/repellent used will be at least an effective amount. The term "effective amount," as used herein, means the minimum amount of the compound needed to cause *Halyomorpha halys* to make oriented movements away from a treated area or object when compared to the same area or object which is untreated. Effective concentrations of the feeding deterrent/repellent in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular feeding deterrent/repellent composition used; the type of area or object to be treated; the number of hours or days of feeding deterring/repelling needed; and the environment in which the area or object is located. The precise amount of feeding deterrent/repellent can easily be determined by one skilled in the art given the teaching of this application. For example, one skilled in the art could follow the procedure utilized below.

The method for repelling *Halyomorpha halys* from an object (e.g., structures) or area (e.g., a surface such as fruit skin) involves treating (or exposing) the object or area with the compounds, and optionally including a carrier material or carrier. The terms "object" or "area" as used herein include any place where the presence of target pests (e.g., *Halyomorpha halys*) is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of fruits and vegetables.

Unless defined otherwise, all technical and scientific terms used herein have the same meaning as commonly understood by one of ordinary skill in the art to which the invention belongs. The term "about" is defined as plus or minus ten percent; for example, about 100° C. means 90° C. to 110° C. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and Methods. Insects Rearing: The *H. halys* colony was established in 2007 from adults collected in Allentown, Pa., and reared on a diet of organic green beans, water (supplied by two 7 cm×2-cm OD test tube)s, and seeds (2:1 sunflower: buckwheat seeds) in plastic containers (21 cm×21 cm OD). Eggs were collected twice weekly throughout the study and put into separate containers containing the same diet. After emerging, the five stages of nymphal instars were reared in the same container until they developed into adult. Within two days after final imaginal ecdysis, a subset of males were separated and reared in different containers for aeration analyses while other adults were held together. Insects were maintained in Thermo Forma chambers (Thermo Fisher Scientific®) at 25° C. and 72% relative humidity with 16L:8D photoperiod. The colony was replenished with ~20 field-collected bugs annually, collected in Beltsville, Md.

Volatile Secretion Compounds Collection and Isolation: Volatile aeration collections were initiated using two-day-old adult virgin males and females held under different densities in a collection device (e.g., 1, 2, 3, 5, 7, 9, and 20 virgin males per group). The males and females were separately placed into two 1-liter, 4-necked glass containers (Zhang, A., et al., Journal of Chemical Ecology, 20: 2415-2427 (1994)). Humidified air was drawn into the container through 6-14 mesh activated charcoal (Fisher Scientific®, Pittsburgh, Pa.) and out through two traps (15 cm×1.5-cm OD) containing Super Q (200 mg each; Alltech Associates, Inc.®, Deerfield, Ill.) by vacuum (~1 liter/min) (Zhang, A., Zeitschrift fur Naturforschung, Section C Biosciences, 57: 553558 (2002)). Insects were fed with organic green beans (replaced every 2-3 days), provided water on cotton balls, and aerated continuously for 20 to 90 days depending on insect living conditions at room temperature (23-25° C.) and 16L:8D photoperiod. The adsorbent traps were changed every day (some of them in 3 days for weekend) and eluted with methylene chloride (0.5 ml/each sample). The elutants were stored in −30° C. freezer until analyses.

Analytical Methods: An Agilent 6890 gas chromatography (GC) equipped with an auto sampler and a 30-m×0.25-mm ID, 0.25-μm film-thickness HP-5MS (J&W Scientific Inc., Folsom, Calif.) capillary column in the splitless mode with hydrogen (1.4 ml/min) as carrier was used for quantitative analysis. A hydrocarbon, 1-tetradecene (10 ng/μl and 1 ng/μl in $CH_2Cl_2$), was used as external standard for quantitative analysis of C-13, while E-2-decenal was analyzed using 5 ng/μl and 10 ng/μl of E-2-decenal. The oven temperature was programmed at 40° C. for 2 min, then heated to 280° C. at 15° C./min and held for 10 min. Electron impact mass spectrometry (EI MS) was conducted on an Agilent 6890 GC coupled to an Agilent 5973 Mass Selective Detector using a 60-m× 0.25-mm ID, 0.25-μm film-thickness DB-WAXETR (J&W Scientific Inc.®, Folsom, Calif.) capillary column at 50° C. for 2 min, then programmed to 250° C. at 15° C./min and held for 15 min or a 60-m×0.25-mm ID, 0.25-μm film-thickness DB-5MS capillary column (50° C. for 2 min, then programmed to 280° C. at 20° C./min and held for 15 min) with helium as carrier gas, unless other temperature programs indicated. A 70 eV electron beam was employed for sample ionization. Chemicals tridecane, E-2-decenal, and Tween-80 were purchased from Sigma-Aldrich® (St. Louis, Mo.) and Bedoukian Research, Inc.®(Danbury, Conn.). Isolongifolenone was synthesized at Beltsville (Wang, S., and A. Zhang, Organic Preparations and Procedures International, 40: 405-410 (2008)) and isolongifolanone was provided by International Flavors & Fragrances Inc. (New York, N.Y.) as a gift.

Optimized petri dish bioassays: Insects tested were moved in groups from Thermo Forma cages to plastic petri dishes for food and water deprivation 16-20 hours before bioassays. Adults were separated by age and sex and held in groups of five, nymphs were held in groups of 20. Bioassays were conducted from April-June of 2012 between 8 a.m. and 4 p.m., in a fume hood lined with black paper and covered with black curtain to prevent external visual stimuli. The fume hood was illuminated by a single 60 watt light bulb with a light intensity of 800 LUX, placed 50 cm above bio assay arenas, with 26°-28° C. temperature and 50% relative humidity. Glass petri dishes (10 cm diameter) were used for the bioassay arena and were lined with Whatman's #1 filter paper (9 cm) that was changed before each assay. Adults were bioassayed individually. Nymphs were tested in groups of four because in preliminary assays they were observed continually walking for up to four hours unless conspecifics were present.

We tested the effects of solvent on *H. halys* survival and feeding behavior to optimize the solvent used in petri dish assays. Mortality of $3^{rd}$ stage nymphs, and adult males and females (ages 3-7 days or 13-23 days into adult stage), was quantified as the percentage of individuals who died after exposure to methylene chloride (DCM) after 2.25 hours. Since young adult males were the most susceptible to DCM, they were tested in bioassays for feeding aversion to four additional solvents (acetone, pentane, hexane, and ethanol). Insects were starved for 16-20 hours prior to being exposed to 1 inch cut sections of organic green beans in a 10 cm petri covered glass petri dish. One bean was coated with 350 solvent while the other was untreated. Behaviors of young adult male individuals were recorded at three time points (45, 90, and 135 minutes) as feeding on the blank (untreated) bean, feeding on the odor (solvent-treated) bean, or sitting on the wall of the petri dish. Percent response for each choice was averaged over the three time periods.

We then used the optimized solvent (i.e., pentane) to test the effects of different repellents on deterring *H. halys* feeding on organic green beans in petri dishes. Insects were tested in a glass Petri dish for their attraction/aversion to 1 μg and 100 μg concentrations of isolongifolanone and isolongifolenone (International Flavors and Fragrances, NY), C-13, and E-2-decenal, diluted in pentane. Pure pentane was tested as a control. Whatman's #1 filter paper (9 cm) was placed in petri dish and 2× one-inch diameter impressions were made with a metal circle. One circle was treated with 75 ul of pentane (control) and the other with pentane+repellant (treatment) and dried for five minutes. One-inch sections of organic green beans were placed over the treated or untreated circle. Starved insects were introduced to the petri dish assay arena and observed at three time points in 45 minute increments for 2.25 hours. Their location was recorded as feeding with stylet inserted on the treatment (i.e., odor) bean, blank bean, or off bean (i.e., walking off of food source or no movement in petri dish and not on bean). Individuals were only used for one bioassay at the adult or nymphal stage in their lifetime. Petri dishes were rinsed with water daily and baked overnight at 100° C., and were rinsed with acetone after every six uses.

Small Cage Bioassays: Nymphs and adults were tested for effects of feeding deterrents/repellents from islongifolanone, islongifolenone, C-13, and E-2-decenal applied to organic peaches and gala apples in a small cage. Insects were starved for 16 hours prior to experiments before being transferred in groups of 15 (nymphs) or 10 (adults male or female) to two gallon containers containing one treated fruit, and observed hourly for the number of nymphs on the fruit. Experiments were conducted in a fume hood under the same light and heat conditions as above. Different concentrations of isolongifolanone, isolongifolenone, C-13, and E-2-decenal were tested both individually and combined (equal amount of each component), with a final concentration of 70-80 mg/fruit chosen as an effective treatment. Compounds (400 mg) were combined with the emulsifier Tween-80 (2 mg), mixed with water ($H_2O$ 10 ml) in glass vial (20 ml), and sonicated for 20 min. The solution containing emulsifier Tween-80 (2 mg) in 10 ml water was used as control. The emulsified solutions were diluted in 30 ml water ($H_2O$) and then evenly sprayed on the fruit surfaces with 6 oz. spray bottles (The Bottle Crew, West Bloomfield, Mich.) and treated fruits were dried in a fume hood for 5 min. The treatments tested were Isolongifolanone, C-13, E-2-decenal, Isolongifolanone+C-13, Isolongifolanone+Isolongifolenone, E-2-decenal+C-13, Isolongifolenone+C-13, Isolongifolanone+Isolongifolenone+C-13, Isolongifolanone+Isolongifolenone+C-13+E-2-decenal, Tween-80, and distilled water ($H_2O$). Isolongifolenone was not tested individually because it is solid at room temperature and could not form an emulsion.

Statistical Analyses: For aeration analyses, we measured the average pheromone, C-13, and E-2-decenal collected per individual male per day in a month, and tested whether this amount varied by month collected using repeated measures ANOVA and Tukey HSD comparisons of log-transformed data with α=0.05 (JMP®). Average and standard error of the male-produced pheromone, C-13, and aldehyde (E-2-decenal) were calculated for single- and multiple-male chambers. The effect of male *H. halys* density on the amount of the compounds in aeration chambers was analyzed for log-transformed data using repeated measures ANOVA. The relationship between C-13 and the male specific compounds was analyzed via repeated measures ANOVA pairwise correlations of log-transformed data, and the relationship between C-13 and E-2-decenal were analyzed using repeated measures ANOVA of log-transformed data.

Optimized petri dish bioassays were analyzed for each age group, sex, and treatment using Likelihood Ratio tests (JMP®). Percent response for each choice per compound was averaged over the three time periods observed. The likelihood of the three choices was set to the level determined by the pentane control for each age/sex group, and the confidence interval set at 95%. P-values are indicated as follows: *=0.05; =0.01; *=0.001.

Small cage bioassays were analyzed by replicate, treatment, and time using repeated measures ANOVA and multiple comparisons for treatments were tested using Tukeys HSD, Model: Nymphs on Fruit=Treatment, Rep (Treatment), Time, Treatment*Time. Letters above bars indicate significance of treatment relative to other treatments at p=0.05; shared letters are not significantly different from each other.

Figure 1:
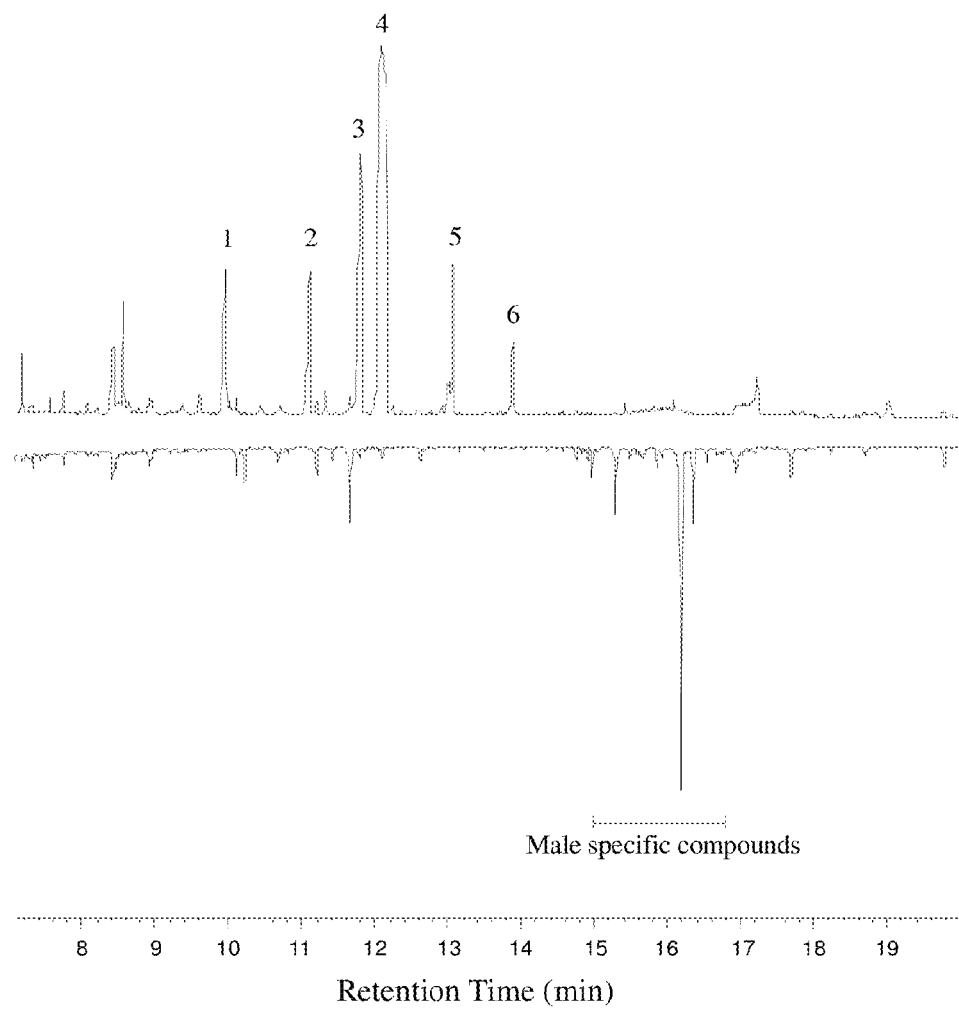
FIG. 1 shows GC/MS total ion traces of aeration extracts from group *H. halys* (top, 17 males) versus individual (bottom, 1 male) on a DB-5MS column as described below. The aerations were conducted using 30 day-old males on May 2, 2011 for 24 hours. Six compounds are indicated: (1) 2-nonanone, (2) C-12 (dodecane), (3) E-2-decenal, (4) C-13 (tridecane), (5) E-2-decenyl acetate, and (6) 2-tridecanone.
Figure 2:
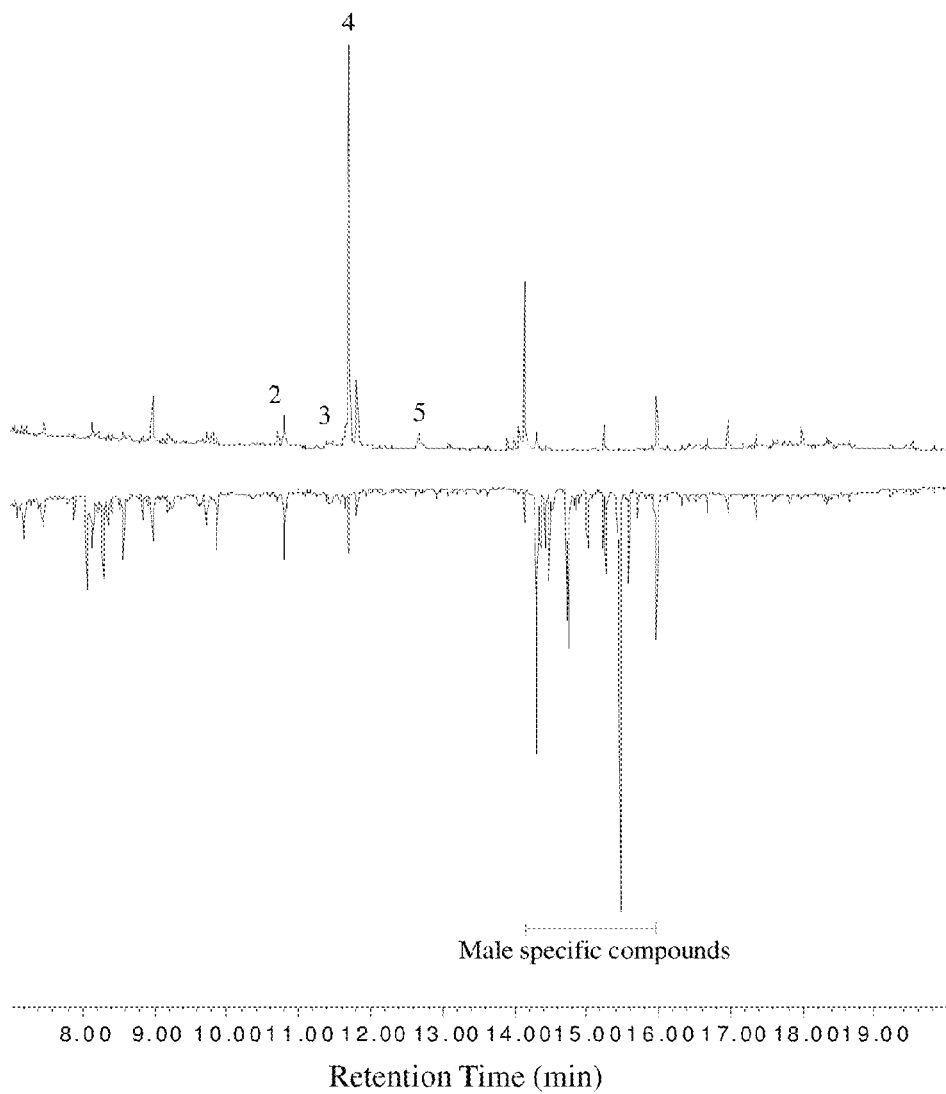
FIG. 2 shows GC/MS total ion traces of aeration extracts from individual female *H. halys* (top) versus male (bottom) on a DB-5MS column as described below. The aerations were conducted using 13 day-old *H. halys* on Oct. 25, 2010 for 24 hours. Four compounds are indicated: (2) C-12, (3) E-2-decenal, (4) C-13, and (5) E-2-decenyl acetate.

Results: The GC/MS total ion traces of airborne extracts from group and single male *H. halys* are shown in FIG. 1. Tridecane (4) and E-2-decenal (3) were surprisingly the major components emitted by the group (top) compared with individual male (bottom). Other minor components, including 2-nonanone, dodecane, E-2-decenyl acetate, and 2-tridecanone, varied by amount in different volatile collections; surprisingly, these compounds were virtually undetectable in the airborne extracts obtained from single males, with male-specific compounds appearing as the major components (bottom). In addition, surprisingly, tridecane was the only major volatile component emitted by individual female *H. halys* compared to individual males (FIG. 2).

Figure 3:
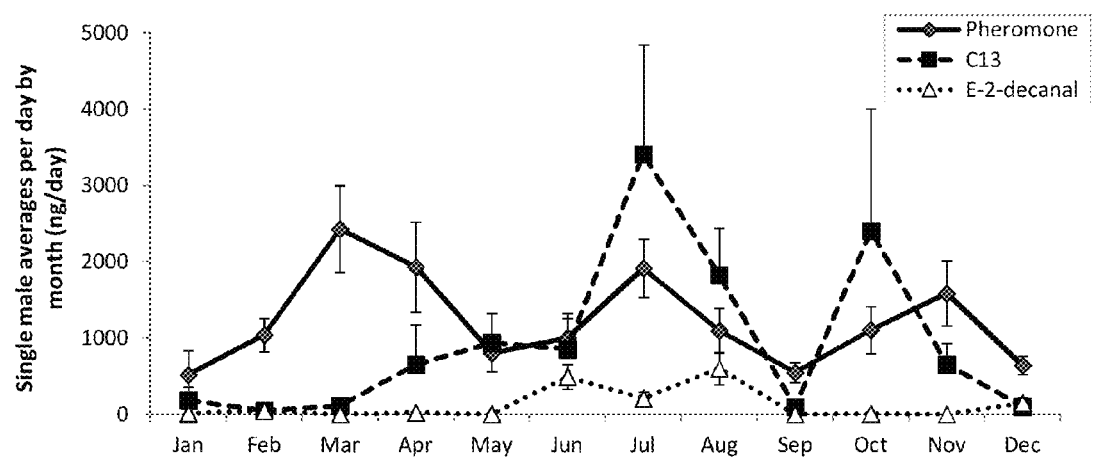
FIG. 3 shows the average male-specific compounds (pheromone), E-2-decenal, and C-13 per chamber by month as described below. Data was collected in 24-hour increments throughout 2011 and 2012 using 13-90 day-old adult male *H. halys*, and was analyzed per individual male per day in a month using ANOVA and Tukey HSD comparisons of log-transformed data with $\alpha=0.05$ (JMP®). ANOVA model of square root-transformed data: Amount of Emission=Compound, Month Started (Year), Year. $R^2$-0.21, ANOVA: $F_{19,389}$-5.192, $p<0.0001$; Compound: F-7.757, p=0.001; Month Started (year): F-5.169, $p<0.0001$; Year: F-3.118, p=0.078.

Average amount of C-13, E-2-decenal, and male-specific compound (pheromone) emission per individual per day was determined for each month of collections (FIG. 3). Adult males emitted more pheromone per day in March than December and January, more C-13 per day in August than in January and February, and more E-2-decenal per day in June than in March, May, and November. Whole model ANOVA: Square root (Amount of Emission)=Compound, Month Started (Year), Year. $R^2$-0.21, ANOVA: $F_{19,389}$-5.192, p<0.0001; Compound: F-7.757, p=0.001; Month Started (year): F-5.169, p<0.0001; Year: F-3.118, p=0.078. ANOVA by compound: Square Root (Compound)=Month Started (Year), Year as follows: For Pheromone, $R^2$-0.354, $F_{17,141}$-3.997, p<0.0001; Month Started (year): F-4.070, p<0.0001; Year: F-0.344, p=0.559. For C-13, $R^2$-0.337, $F_{15,123}$-3.653, p<0.0001; Month Started (year): F-3.752, p<0.0001; Year: F-2.701, p=0.103. For E-2-decenal, $R^2$-0.497, $F_{16,67}$-3.150, p=0.001; Month Started (year): F-1.211, p=0.295; Year: F-4.397, p=0.041.

Figure 4A:
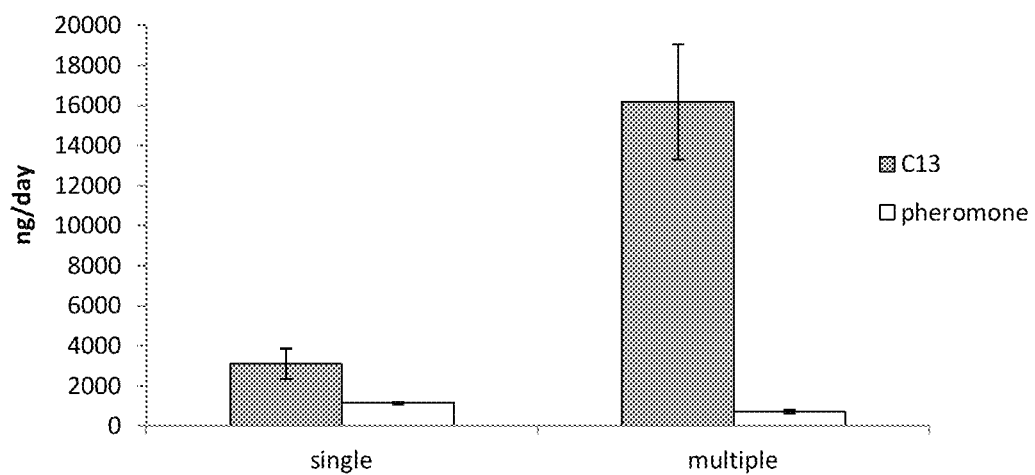
FIG. 4A shows data for average male specific compounds and C-13 per day for single v. multiple males. C-13: $F_{71,1}$=4.256; p=0.003; Male specific compounds: $F_{71,1}$=6.634; p<0.0001.
Figure 4B:
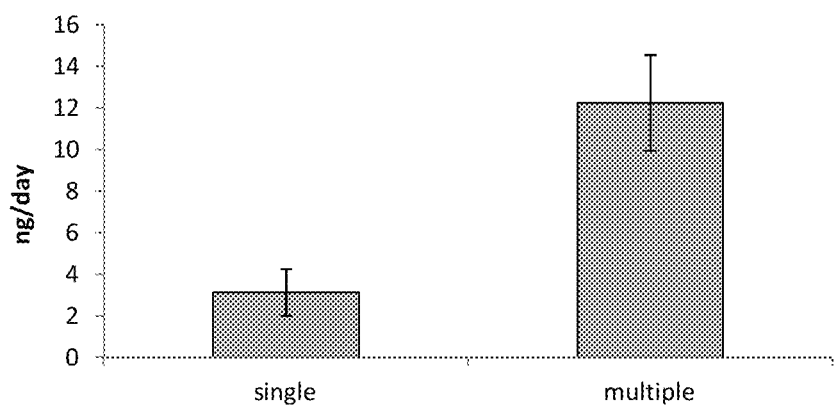
FIG. 4B shows data for average E-2-decenal per day for single v. multiple males. Aldehyde: $F_{71,1}$=3.070; p=0.003.

*H. halys* males surprisingly produced significantly more C-13 when held in groups of two or more than when held individually (FIG. 4A); $F_{71,1}$=4.256; p=0.003. Conversely, male-specific compound (pheromone) emission was surprisingly lower for groups of males than those held individually $F_{71,1}$=6.634; p<0.0001. Surprisingly, *H. halys* males produced significantly more of the defensive aldehyde when held in groups of two or more than when held individually (FIG. 4B); $F_{71,1}$=3.070; p=0.003.

The concentration of C-13 and aldehyde surprisingly increased proportionately as the number of males increased, while the amount of male-specific compounds emitted surprisingly decreased (FIG. 5); Pheromone=subject, #males (subject): $F_{71,1}$-6.634; p<0.0001; C-13=subject, # males (subject): $F_{71,1}$-5.701; p=0.001; Aldehyde=subject, # males (subject): $F_{71,1}$=1.617; p=0.003. Regression equations: Pheromone=−0.17×+2.52; C-13=0.22×+1.15; Aldehyde=−0.773×+0.290. Multivariate pairwise correlations p<0.0001. The C-13 and male-specific compounds interaction overlapped at 2.5 males. Groups of males began releasing C-13 nine days post-imaginal ecdysis and release in cyclic bursts throughout their adulthood.

Surprisingly, different solvents had different effects on *H. halys* behavior. When 35 µl of solvent was applied to a fresh 1-inch section of green bean, starved adult males ages (3-7 days) were significantly less likely to feed on beans treated with methylene chloride (DCM), hexane, or acetone. Less feeding aversion was seen for beans treated with 35 ul ethanol. Young adult males showed a slight preference for pentane-treated green beans over the untreated control bean. Based on these results, we chose pentane as the solvent for our subsequent repellent assays in petri dishes.

Figure 6A:
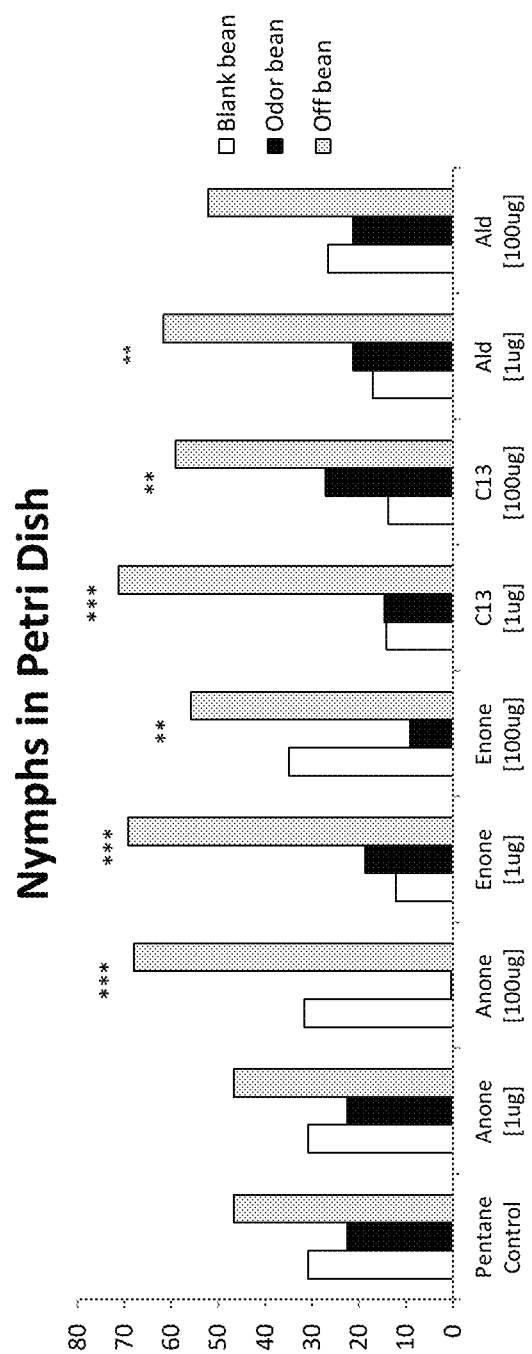
Figure 6C:
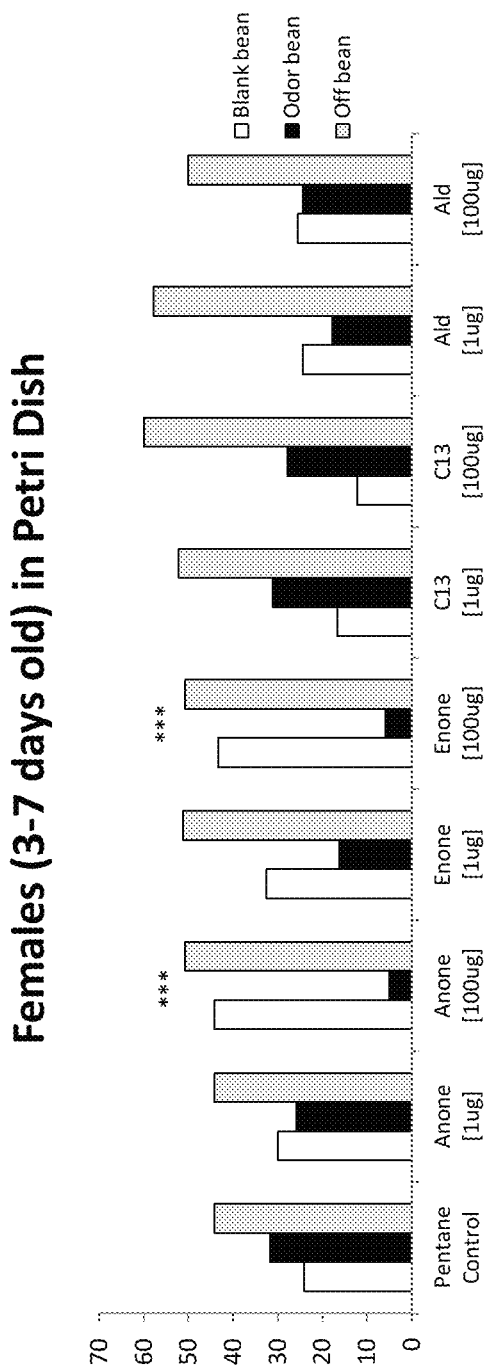
Figure 6D:
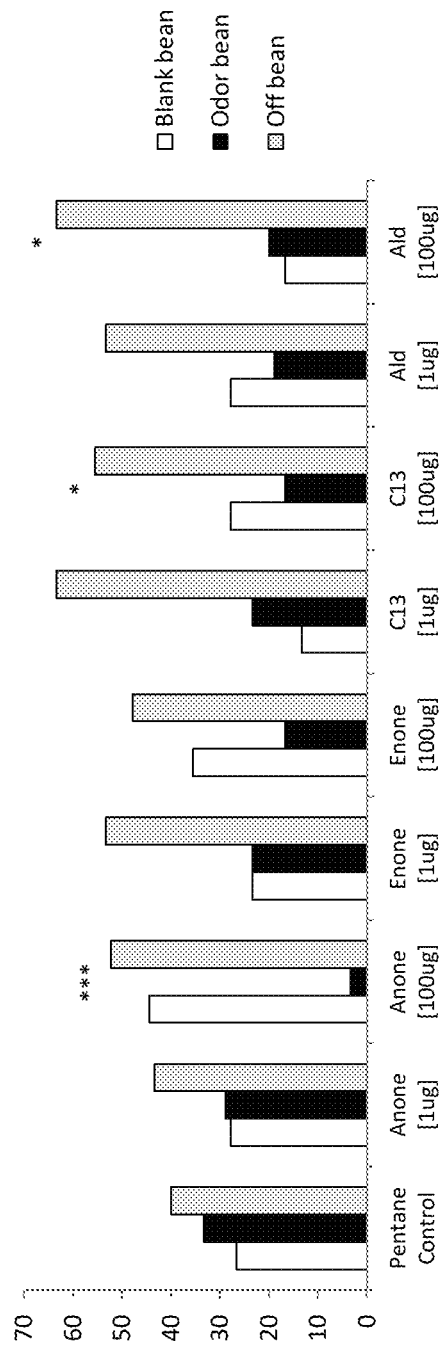
Figure 6E:
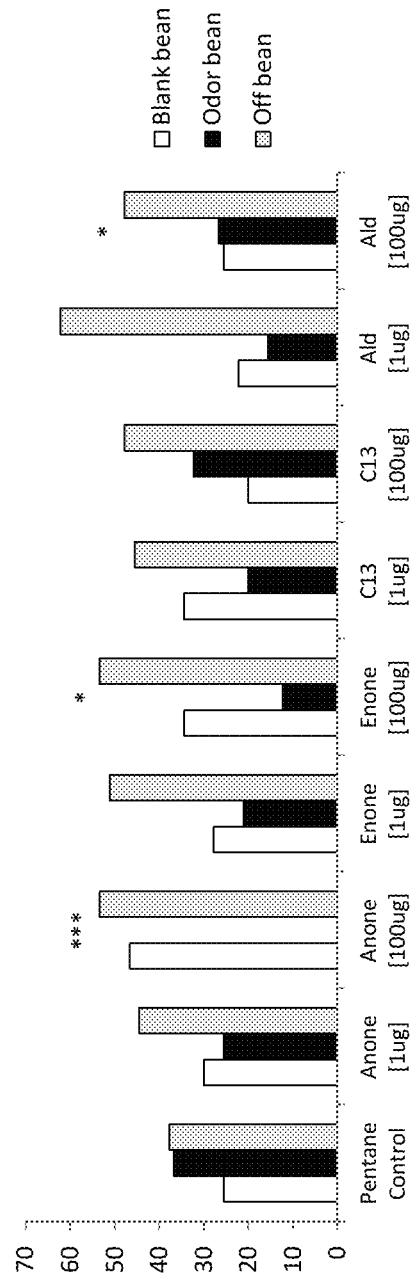

In closed-air optimized bioassays, starved nymphs ($3^{rd}$ stage) were significantly less likely to feed on beans treated with 100 µg isolongifolanone, as well as 1 µg or 100 µg concentrations of isolongifolenone and C-13 (FIG. 6A). Young adult males (ages 3-7 days into adult stage) were significantly less likely to feed on 100 µg concentrations of isolongifolanone, isolongifolenone, and C-13, as well as 1 µg E-2-decenal (FIG. 6B), and young adult females were deterred by 100 µg concentrations of isolongifolanone and isolongifolenone (FIG. 6C). Old adult males (ages 13-23 days) were significantly less likely to feed on beans treated with 100 µg isolongifolanone or 1 µg C-13 (FIG. 6D), and old adult females were deterred by 100 µg concentrations of isolongifolanone and isolongifolenone (FIG. 6E). For nominal logistic regression statistical analysis of all compounds by age group (Model: age group response=Compound), the likelihood ratio statistics were as follows: Nymph $\chi^2$-72.047, p<0.0001; Young Adult Male $\chi^2$-33.697, p=0.006; Young Adult Female $\chi^2$-31.446, p=0.012; Old Adult Male $\chi^2$-18.947, p=0.167; Old Adult Female $\chi^2$-20.021, p=0.130. Asterisks above groups of bars indicate the significance of the three behavioral observations (blank bean, odor bean, off bean) relative to the pentane control shown as the first set of bars in the figure, with p<0.05 (*), p<0.01 (), and p<0.001 (*), n=30-40 for adults, 40-80 for nymphs.

Table 1 summarizes the results for compounds and concentrations tested in optimized petri dish assays from FIGS. 6A-E. Isolongifolanone at 100 µg concentration was significantly repellent to all age groups and sexes. Isolongifolenone at 100 µg concentration was the next most effective, deterring all groups except for old adult males. C-13 was the next most effective and was deterrent to young males and old adult males and nymphs. E-2-decenal 1 µg was effective at deterring Nymphs, young adult males, and old adult females, while E-2-decenal 100 µg was effective at deterring old adult males. Boxes indicated with n.s. mean that compound tested was not significant in repelling insect from treated bean.

FIGS. 7A-D show the effectiveness of both individual and combined compounds at deterring $H.$ $halys$ feeding in small cage bioassays. Letters above bars indicate significance of treatment relative to other treatments; shared letters are not significantly different from each other. The average number of nymphs ($3^{rd}$ stage) feeding on peaches over 8 hours of observations was lower for all compounds and combinations of compounds relative to the Tween and $H_2O$ controls, except for the aldehyde/C-13 combination (FIG. 7A). The three-component blend of equal concentrations isolongifolanone+isolongifolenone+C-13 yielded the highest repellency. Statistical analysis of ANOVA (Model: Insects on fruit=Treatment, Rep (Treatment) were as follows: For nymphs: $F_{10,830}$-41.82, p<0.0001. Nymphs were tested in groups of 15 individuals, with 4-28 reps per treatment.

Male and female behavior in small cages was observed for repellents on peaches (FIG. 7C) and apples (7D), and did not significantly differ by fruit or age group tested (see detailed statistical model below), so data was combined in FIG. 7B. The 3- and 4-component blends of isolongifolanone+isolongifolenone+C-13, and isolongifolanone+isolongifolenone+C-13+Aldehyde were significantly more repellent to starved male and female adults than the Tween and $H_2O$ control. C-13 and Anone/C-13 were not tested for adults in apples. We used repeated-measures ANOVA to test the following model: Number of $H.$ $halys$ on fruit=Treatment, Sex, Time (Treatment), Rep (Treatment), Age, Time*Treatment. There was a significant effect for treatment in peaches (p<0.0001) and apples (p<0.0001), and a significant effect for time in apples (p<0.0001). For the same test run on combined apples and peaches data, there was a significant effect for treatment (p=0.007) and time (p<0.0001), but not for fruit. The significant effect of time indicated that the deterrent properties of the tested repellents wore off in open cage systems several hours after their application to the food source. There were 10 male or female adults per cage and 2-6 reps conducted per sex (4-12 reps total).

Discussion: From $H.$ $halys$ airborne collection extracts, we found that groups of males surprisingly produced significantly more C-13 and E-2-decenal than single individuals (FIGS. 1 and 4), indicating that communication between males could influence the emission rate of the semiochemicals. Bug density having an effect on emission rate of defensive compounds has not been previously reported in the Pentatomid family of insects. Our results clearly show that the amounts of C-13 and E-2-decenal were positively proportional to the number of the males (FIG. 5). Thus, higher densities of males yielded higher amounts of C-13 and E-2-decenal. Conversely, male-specific semiochemicals (pheromone) were severely reduced, or absent, when C-13 and the defensive aldehyde were present in aeration analyses (FIG. 5). These results suggest that high densities are not profitable environment for mate-seeking males, so that males produce more tridecane and E-2-decenal to repel conspecific males away in order to maintain an optimal population density in their habitat. We confirmed the repellency of C-13 by showing that it deterred $H.$ $halys$ feeding when diluted in pentane, a solvent that was slightly attractive to $H.$ $halys$ feeding (FIGS. 6a-6e). The decreased repellency of C-13 in small cage tests was likely due to the high evaporation rate of this compound in open-air systems and we are currently optimizing the longevity of C-13.

Based on the above information, we conclude that tridecane (i.e., C-13), a hydrocarbon from the $H.$ $halys$ secretion, not only acts as a defensive odor carrier, but also is a semiochemical component that has significant biological function to influence $H.$ $halys$ behavior. To our knowledge, no applications of using tridecane and E-2-decenal in insect pest management have been previously reported. Furthermore, based on the information above, we found that isolongifoloanone and isolongifolenone were highly effective repellents for deterring all age groups and sexes of $H.$ $halys$, especially when combined with their natural semiochemical secretions C-13 and E-2-decenal.

The effectiveness of various insecticide classes to control of $H.$ $halys$ have been tested in laboratory conditions (Nielsen, A. L., et al., Journal of Economic Entomology, 101: 1439-1442 (2008); however, some pesticide application must be conducted by a pest control applicator and causes additional cost/time to growers. An egg parasitoid, $Trissolcus$ $halymorphae$ Yang (Hymenoptera: Scelionidae), is a biological control agent of $H.$ $halys$ currently used in northern China (Yang, Z. Q., et al., Annals of the Entomological Society of America, 102: 39-47 (2009). Although it has a potential as a biocontrol agent to be used in the U.S., it still is under risk assessment and evaluation. We have identified isolongifolanone, isolongifolenone, tridecane, and E-2-decenal as feeding deterrents/repellents of $H.$ $halys$ male and nymph, and they can be immediately used for management of $H.$ $halys$ populations in orchards or other commodity-based fields.

Because they are natural products, there are no environmental pollution concerns related to using synthetic insecticides. These identified feeding deterrents/repellents are commercially available and can be easily commercialized as different formulations and used for protecting agricultural crops from *H. halys* damage in support of ongoing *H. halys* management programs.

All of the references cited herein, including U.S. Patents, are incorporated by reference in their entirety. Also incorporated by reference in their entirety are the following references: Aligiannis, N., et al., Flavour and Fragrance Journal, 19: 320-324 (2004); Ashour, M. L., et al., Journal of Pharmacy and Pharmacology, 61: 1079-1087 (2009); Baser, K. H. C., et al., Journal of Essential Oil Research, 18: 515-517 (2006); Borges, M., et al., Entomologia experimentalis et applicata, 44: 205-212 (1987); Brahmi, F., et al., International Journal of Food Science and Technology, 46: 1316-1322 (2011); Calam, D. H., and A. Youdeowei, Journal of Insect Physiology, 14: 1147-1158 (1968); Favaro, C. F., et al., Journal of the Brazilian Chemical Society, 22: 58-64 (2011); Fons, F., et al., Natural Product Communications, 5: 1655-1658 (2010); Fucarino, A., et al., Journal of Chemical Ecology, 30: 1257-1269 (2004); Gough, A. J. E., et al., Journal of Chemical Ecology, 11: 343-352 (1985); Ho, H. Y., and J. G. Millar, Zoological Studies, 40: 193-198 (2001); Ho, H. Y., et al., Journal of Chemical Ecology, 29: 2101-2114 (2003); Ho, H. Y., et al., Journal of Chemical Ecology, 31: 29-37 (2005); Kou, R., et al., Journal of Chemical Ecology, 15: 2695-2702 (1989); Krall, B. S., et al., Journal of Chemical Ecology, 25: 2477-2494 (1999); Lockwood, J. A., and R. N. Story, Ann Entomol. Soc. Am., 78: 474-479 (1985); Marques, F. A., et al., Journal of the Brazilian Chemical Society, 18: 1242-1246 (2007); Moronkola, D. O., et al., Journal of Essential Oil Research, 21: 264-266 (2009); Ortiz Moreno, A., et al., Journal of Agricultural and Food Chemistry, 51: 2216-2221 (2003); Nagalakshmi, M. A. H., et al., Flavour and Fragrance Journal, 16: 241-244 (2001); Nagnan, P., et al., International Journal of Insect Morphology and Embryology, 23: 355-370 (1994); Pareja, M., et al., Journal of Insect Physiology, 53: 639-648 (2007); Rapior, S., et al., Journal of Essential Oil Research, 8: 199-201 (1996); Raspotnig, G., et al., Experimental and Applied Acarology, 25: 933-946 (2001); Sosa-Gomez, D. R., et al., Journal of Invertebrate Pathology, 69: 31-39 (1997); Sturaro, A., et al., Chromatographia, 39: 103-106 (1994); Telci, I., and Y. Hisil, European Journal of Horticultural Science, 73: 267-272 (2008); Tu, N. T. M., et al., Flavour and Fragrance Journal, 17: 169-174 (2002); Wang, J., et al., Natural Product Communications, 6: 1749-1753 (2011); Williams, L., III, et al., Journal of Chemical Ecology, 27: 203-216 (2001); Witte, V., et al., Chemoecology, 17: 63-69 (2007); Zahn, D. K., et al., Journal of Chemical Ecology, 34: 238251 (2008); U.S. Pat. No. 7,378,557; U.S. Pat. No. 7,579,016.

Thus, in view of the above, the present invention concerns (in part) the following:

A composition comprising (or consisting essentially of or consisting of) at least two compounds selected from the group consisting of tridecane, E-2-decenal, isolongifolanone, isolongifolenone, and at least one isolongifolenone analog having the following formula:

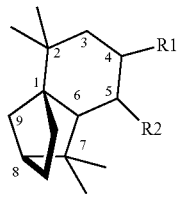

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. The composition may contain any combination of the compounds so long as at least two of the compounds are present.

The above composition, wherein said composition comprises at least three compounds selected from the group consisting of E-2-decenal, tridecane, isolongifolanone, isolongifolenone, and at least one isolongifolenone analog having the following formula:

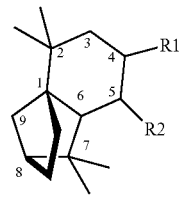

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The composition may contain any combination of the compounds so long as at least three of the compounds are present.

The above composition, wherein said composition comprises at least four compounds selected from the group consisting of E-2-decenal, tridecane, isolongifolanone, isolongifolenone, and at least one isolongifolenone analog having the following formula:

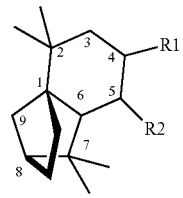

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The composition may contain any combination of the compounds so long as at least four of the compounds are present.

The above composition, wherein said composition comprises E-2-decenal, tridecane, isolongifolanone, isolongifolenone, and at least one isolongifolenone analog having the following formula:

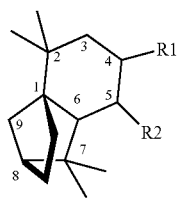

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

The above composition, wherein said composition contains E-2-decenal. The above composition, wherein said composition does not contain E-2-decenal.

The above composition, wherein said composition contains tridecane. The above composition, wherein said composition does not contain tridecane.

The above composition, wherein said composition contains isolongifolanone. The above composition, wherein said composition does not contain isolongifolanone.

The above composition, wherein said composition contains isolongifolenone. The above composition, wherein said composition does not contain isolongifolenone.

The above composition, wherein said composition contains at least one isolongifolenone analog having the following formula:

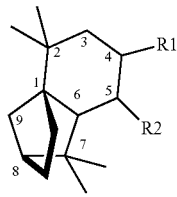

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The above composition, wherein said composition does not contain at least one isolongifolenone analog having the following formula:

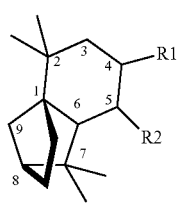

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

The above composition, wherein said composition contains tridecane and E-2-decenal.

A method for deterring feeding/repelling *Halyomorpha halys*, said method comprising (or consisting essentially of or consisting of) treating an object or area with a composition comprising (or consisting essentially of or consisting of) a *Halyomorpha halys* deterring feeding/repelling effective amount of at least one compound selected from the group consisting of tridecane, E-2-decenal, isolongifolanone, isolongifolenone, and at least one isolongifolenone analog having the following formula:

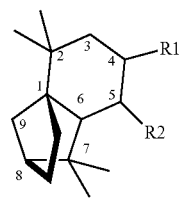

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material. The composition may contain any combination of the compounds so long as at least one of the compounds are present.

The above method, wherein said composition comprises at least two compounds selected from the group consisting of E-2-decenal, tridecane, isolongifolanone, isolongifolenone, and at least one isolongifolenone analog having the following formula:

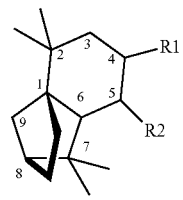

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The composition may contain any combination of the compounds so long as at least two of the compounds are present.

The above method, wherein said composition comprises at least three compounds selected from the group consisting of E-2-decenal, tridecane, isolongifolanone, isolongifolenone, and at least one isolongifolenone analog having the following formula:

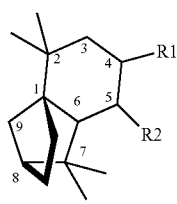

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The composition may contain any combination of the compounds so long as at least three of the compounds are present.

The above method, wherein said composition comprises at least four compounds selected from the group consisting of E-2-decenal, tridecane, isolongifolanone, isolongifolenone, and at least one isolongifolenone analog having the following formula:

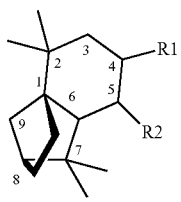

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The composition may contain any combination of the compounds so long as at least four of the compounds are present.

The above method, wherein said composition comprises E-2-decenal, tridecane, isolongifolanone, isolongifolenone, and at least one isolongifolenone analog having the following formula:

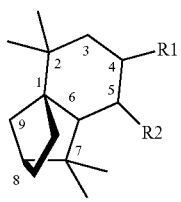

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

The above method, wherein said composition contains E-2-decenal. The above method, wherein said composition does not contain E-2-decenal.

The above method, wherein said composition contains tridecane. The above method, wherein said composition does not contain tridecane.

The above method, wherein said composition contains isolongifolanone. The above method, wherein said composition does not contain isolongifolanone.

The above method, wherein said composition contains isolongifolenone. The above method, wherein said composition does not contain isolongifolenone.

The above method, wherein said composition contains at least one isolongifolenone analog having the following formula:

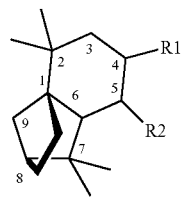

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen. The above method, wherein said composition does not contain at least one isolongifolenone analog having the following formula:

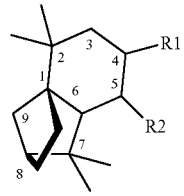

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

The above method, wherein said composition contains tridecane and E-2-decenal.

The above method, wherein said composition contains tridecane and E-2-decenal in a 10:1 molar ratio.

The above method, wherein said *Halyomorpha halys* is selected from the group consisting of males, females, and mixtures thereof.

The above method, wherein said *Halyomorpha halys* are males.

The above method, wherein said *Halyomorpha halys* are females.

The above method, wherein said *Halyomorpha halys* are in an immature stage (e.g., nymphs).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

|  | Anone | | C13 | | Enone | | E-2-decenal | |
| --- | --- | --- | --- | --- | --- | --- | --- | --- |
|  | 1 µg | 100 µg | 1 µg | 100 µg | 1 µg | 100 µg | 1 µg | 100 µg |
| Nymph |  | *** | *** | ** | *** | ** | ** | n.s. |
| Young Adult Male |  | *** | n.s. | * | n.s. | *** | ** | n.s. |
| Young Adult Female |  | *** | n.s. | n.s. | n.s. | *** | n.s. | n.s. |
| Old Adult Male |  | *** | n.s. | * | n.s. | n.s. | n.s. | * |
| Old Adult Female |  | *** | n.s. | n.s. | n.s. | * | n.s. | * |

We claim:

1. A composition for deterring feeding/repelling *Halyomorpha halys*, said composition consisting of tridecane, (E)-2-decenal, (a) optionally at least one compound selected from the group consisting of isolongifolanone, and isolongifolenone, and (b) at least one isolongifolenone analog having the following formula:

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen; and optionally a carrier or carrier material.

* * * * *